US007867720B2

(12) United States Patent
Dodds

(10) Patent No.: US 7,867,720 B2
(45) Date of Patent: *Jan. 11, 2011

(54) FOOD SENSITIVITY TESTING IN ANIMALS

(76) Inventor: W. Jean Dodds, 938 Stanford St., Santa Monica, CA (US) 90403

( * ) Notice: Subject to any disclaimer, the term of this patent is extended or adjusted under 35 U.S.C. 154(b) by 0 days.

This patent is subject to a terminal disclaimer.

(21) Appl. No.: 12/465,603

(22) Filed: May 13, 2009

(65) Prior Publication Data

US 2010/0190190 A1 Jul. 29, 2010

Related U.S. Application Data

(60) Provisional application No. 61/147,443, filed on Jan. 26, 2009.

(51) Int. Cl.
*G01N 33/53* (2006.01)
(52) U.S. Cl. .................. 435/7.1; 435/7.92; 436/513; 436/811
(58) Field of Classification Search .................. None
See application file for complete search history.

(56) References Cited

U.S. PATENT DOCUMENTS

| 4,487,830 | A * | 12/1984 | Coates et al. .............. 435/7.23 |
|---|---|---|---|
| 6,287,254 | B1 | 9/2001 | Dodds |
| 6,537,213 | B2 | 3/2003 | Dodds |
| 6,689,569 | B2 | 2/2004 | Vojdani |
| 6,730,023 | B1 | 5/2004 | Dodds |
| 6,858,398 | B2 | 2/2005 | Vojdani |
| 7,029,441 | B2 | 4/2006 | Dodds |
| 7,134,995 | B2 | 11/2006 | Dodds |
| 7,296,537 | B2 | 11/2007 | Burghardi et al. |
| 2002/0022772 | A1 | 2/2002 | Dodds |
| 2003/0135096 | A1 | 7/2003 | Dodds |
| 2003/0233984 | A1 | 12/2003 | van de Ligt et al. |
| 2005/0090718 | A1 | 4/2005 | Dodds |
| 2005/0255533 | A1 | 11/2005 | Dantini et al. |
| 2006/0045909 | A1 | 3/2006 | Friesen et al. |
| 2006/0200320 | A1 | 9/2006 | Al-Murrani |
| 2009/0132465 | A1 | 5/2009 | Dodds |
| 2009/0253154 | A1* | 10/2009 | Vojdani ..................... 435/7.92 |

FOREIGN PATENT DOCUMENTS

WO    WO 99-67642 A2    12/1999

OTHER PUBLICATIONS

Jeffers et al., Diagnostic testing of dogs for food hypersensitivity, JAVMA, vol. 198, No. 2, Jan. 15, 1991, pp. 245-250.*
Van Dijk et al., Gastrointestinal Food Allergy and its Role in Large Domestic Animals, Veterinary Research Communications, 12 (1988), pp. 47-59.*
Foster et al., Serum IgE and IgG responses to food antigens in normal and atopic dogs, and dogs with gastrointestinal disease, Veterinary Immunology and Immunopathology, 92, (2003), pp. 113-124.*
Day., The canine model of dietary hypersensitivity, Proceedings of the Nutrition Society (2005), 64, pp. 458-464.*
Buchanan et al., The Dog as a Model for Food Allergy, Annals New York Academy of Sciences, 964: (2002), pp. 173-183.*
Barratt et al., Immunoglobulin classes implicated in intestinal disturbances of calves associated with soya protein antigens, The Journal of Immunology, vol. 123, No. 2, Aug. 1979.*
Cave et al., Evaluation of the immunogenicity of dietary proteins in cats and the influence of the canning process, American Journal of Veterinary Research, vol. 65, No. 10, Oct. 2004, pp. 1427-1433.*
Flickinger, et al.; Immunoglobulin A Concentrations in Adult Dogs Vary According to Sample Type and Collection Time and Method; Waltham International Science Symposium: Nature, Nurture, and the Case for Nutrition; J. Nutr. 134: 2130S-2132S, 2004; © 2004 American Society for Nutritional Sciences; Department of Animal Sciences, University of Illinois, Urbana, IL 61801.
Rinkinen, et al.; Relationship between canine mucosal and serum immunoglobulin A (IgA) concentrations: serum IgA does not assess duodenal secretory IgA; PubMed; 2003; 47(2): 155-9; U.S. National Library of Medicine National Institutes of Health; Department of Clinical Veterinary Sciences, Faculty of Veterinary Medicine, Helsinki University, P.O. Box 57, 00014; http://www.ncbi.nlm.nih.gov/pubmed/12680719.
German, et al.; Measurement of IgG, IgM and IgA concentrations in canine serum, saliva, tears and bile; Veterinary Immunology and Immunopathology; 1998; 107-121; Department of Clinical Veterinary Science, University of Bristol, Langford, Bristol BS40 5DU, UK; Department of Pathology and Microbiology, University of Bristol, Langford, Bristol BS40 5DU, UK.
Heddle, et al.; I. Immunochemical Characterization of Dog Serum, Parotid Saliva, Colostrum, Milk and Small Bowel Fluid; Dog Immunoglobulins; 1975; 185-195; 29; Department of Microbology, The University of Adelaide, Adelaide, Australia.
Tizard, Ian; Antibodies; Veterinary Immunology An Introduction; 1992; 115; Fourth Edition; W.B. Saunders Company, Harcourt Brace Jovanovich, Inc., Philadelphia, London, Toronto, Montreal, Sydney, Tokyo.

(Continued)

*Primary Examiner*—Melanie Yu
*Assistant Examiner*—Gary W Counts
(74) *Attorney, Agent, or Firm*—Greenberg Traurig LLP

(57) ABSTRACT

Diagnosing an immunologic food sensitivity or intolerance in companion animals comprises collecting a sample; screening the sample to detect the presence of an antibody to a particular food ingredient or composition. The sample can be serum, saliva or other bodily fluid to detect the presence of an IgA, IgM or IgG antibody or immune complex to a particular food ingredient or composition. The food ingredient for which sensitivity or intolerance is tested is contained in at least one of a preprocessed food composition, balanced diet or recipe. Offending ingredient(s) in a preprocessed food composition, balanced diet or recipe is determined. An assessment is made as to whether it is possible to use a different preprocessed food composition, balanced diet or recipe, or whether a special diet needs to be formulated without the offending ingredient(s).

15 Claims, No Drawings

OTHER PUBLICATIONS

Delacroix, et al.; Quantitative Relationships of Monomeric and Polymeric Immunoglobulin A, Immunoglobulin M, and Other Proteins in Serum, Bile, and Saliva; Selective Transport of Polymeric Immunoglobulin A in Bile; Aug. 1982; 230-241; vol. 70; J. Clin. Invest. © The American Society for Clinical Investigations, Inc.

Tizard, Ian; Immunity at Body Surfaces; Vertinary Immunology An Introduction; 1992; 242; Fourth Edition; W.B. Saunders Company, Harcourt Brace Jovanovich, Inc., Philadelphia, London, Toronto, Montreal, Sydney, Tokyo.

M.F. Bottcher, M.F. et al., (Total and allergen-specific immunoglobulin A levels in saliva in relation to the development of allergy in infants up to 2 years of age) Clin. Exp. Allergy Sep. 2002, vol. 32, No. 9, pp. 1293-1298.

* cited by examiner

FOOD SENSITIVITY TESTING IN ANIMALS

RELATED APPLICATIONS

This Application claims priority from Application Ser. No. 61/147,443 filed on Jan. 26, 2009, entitled FOOD SENSITIVITY TESTING IN ANIMALS (Dodds). This application is concerned with and relates to the disclosure of DIAGNOSTIC SYSTEM FOR SELECTING NUTRITION AND PHARMACOLOGICAL PRODUCTS FOR ANIMALS, filed as application Ser. No. 12/316,824 on Dec. 16, 2008. This application is also concerned with and relates to the disclosure of DETECTION AND MEASUREMENT OF THYROID HORMONE AUTOANTIBODIES, filed as application Ser. No. 12/269,866 on Nov. 12, 2008 (Dodds and Ongchangco). This application is also concerned with and relates to the disclosure of DETECTION AND MEASUREMENT OF THYROID HORMONE AUTOANTIBODIES USING EQUILIBRIUM DIALYSIS, filed as application Ser. No. 61/156,843 on Mar. 2, 2009 (Dodds and Ongchangco). This application is also concerned with and relates to the disclosure of DETECTION AND MEASUREMENT OF THYROID ANALYTE PROFILE, filed as application Ser. No. 12/430,038 on Apr. 24, 2009 (Dodds and Ongchangco). The contents of all these applications are incorporated by reference herein.

BACKGROUND

The present disclosure is directed to food sensitivity testing in companion animals.

A common health concern identified by health surveys of several purebred dog clubs is food sensitivity or intolerance. Other than time-consuming feeding trials, which eliminate potential allergic ingredients every several weeks, testing for this disorder uses expensive and unsightly skin patch testing or serum allergy screening that lack specificity.

Delayed food sensitivities in people are extremely common and can be manifested by gastrointestinal, neurological, pulmonary, dermatologic, ear, nose and throat, musculoskeletal, genitourinary, cardiovascular and endocrine problems. Similar clinical problems are manifested in animals with food sensitivities.

Diagnostic testing systems available for humans are typically based on either immunoglobulin E (IgE) or immunoglobulin A (IgA) or a combination of immunoglobulin G (IgG) antibody or immune complex testing mediated by complement.

The newer test methodologies for humans are run on serum, feces, or saliva and typically use ELISA or other immunoassay platforms such as lateral flow, or latex or bead agglutination, and identify IgG or IgA or immune complex reactions to food ingredients that are mediated by complement, as well as IgA or immunoglobulin M (IgM) antibodies to food ingredients that are elaborated in saliva.

Research has shown that the key to delayed or latent or pre-clinical food sensitivity testing in humans is the identification of the offending IgG or IgA antibodies and immune complexes in serum or feces, and the offending IgA or IgM antibodies in saliva. In fact, antibodies to food ingredients can appear in the saliva before the clinical or gastrointestinal biopsy diagnosis of inflammatory bowel disease or "leaky gut syndrome" is made in human patients. Saliva testing can thus reveal the latent or pre-clinical form of food sensitivity. A similar elaboration of IgA or IgM antibody in saliva but not serum pertains to animals with latent or pre-clinical gastrointestinal disease.

Delayed sensitivities in humans are usually revealed as soon as 2 hours or as long as 72 hours after eating, which is the reason it can be difficult to connect the symptoms with a food or foods eaten as long as several days previously. There is a very high correlation between delayed food sensitivity and the amount and frequency of the food consumed.

In human serum testing, food sensitivity reactions in the gut lead to increased blood levels of IgA or IgG directed to these food ingredients. Similarly, the immune complexes being formed from food reactions in the blood adhere to red blood cells and these altered blood cells are then cleared by the body's recticuloendothelial system in the liver and spleen. Individuals having more immune complex on their red blood cells are the ones who suffer from chronic food sensitivities.

In saliva testing, deposition of food antigens or peptides in the gut has been documented in humans to lead to the production of IgA or IgM antibodies in the serum and in secretions such as saliva. In some situations, IgA or IgM antibodies to food ingredients appear in saliva but are not present in serum. So in humans salivary antibodies serve as an indication of a general mucosal immune response and can be induced in people and animals without parallel antibodies being detected in serum.

There is a need to provide for practical and rapid screening or testing for food sensitivity and intolerance to permit enhancement of the health of animals.

Studies have indicated that specialized nutrient intake extends and improves life, delays onset and slows progression of disease, and enhances the quality of life of companion animals.

Changing the proportions of macro-nutrients and micro-nutrients in different nutrient and food products is important in obtaining the right balance. To date, the utility of such characteristics and components has been limited or not as useful as possible.

Currently, time consuming elimination dietary trials are done where one ingredient at a time is removed and the remaining diet is fed for six to eight weeks to determine if the animal patient's food sensitive or food intolerance symptoms subside. Alternatively, arbitrary selection can be made of a food preparation containing limited, namely restricted antigen source, or novel, namely not fed previously, ingredients(s) are employed. Both these techniques are imprecise or indirect methods of addressing the problem.

The present disclosure provides for screening or testing animal subjects for sensitivity or intolerance relative to dietary compositions, and the testing and screening should be advantageous and commercially useful.

SUMMARY

In accordance with this disclosure there is provided a diagnostic test system for screening or testing for food sensitivity or intolerance in animals, in particular companion animals, such as dogs, cats, rabbits, hamsters, and horses.

Immunglobulins in companion animals differ from those in humans in certain structural and functional aspects in blood, body fluids and tissues. Specifically, cats have significantly more IgA in saliva and serum than dogs or humans, although dogs also have less serum IgA than humans. Levels of IgA and IgM are correlated in dog saliva and tears, but there are conflicting data regarding the correlation between serum and secretary IgA levels in dogs. Further, cats with oral diseases such as gingivitis or stomatitis have increased levels of salivary IgG and IgM but less salivary IgA, whereas serum levels of all three of the immunoglobulins are uniformly increased. Salivary immunoglobulin levels in cats remain relatively constant whereas those of dogs vary from day to day and there may be diurnal variation with higher levels in the afternoon.

Similarly, the salivary and serum IgM levels of dogs and cats are higher in amounts from those of humans.

Saliva can be used as a diagnostic tool to assess the health or disease status of an animal. Saliva is easily collected, stored and shipped, and provides a non-invasive means of multiple or serial sampling for use as a diagnostic tool for a variety of conditions in animals.

The measurement of selected blood (serum) and salivary antibodies is compared in healthy individual animals and in those animals known to have or suspected of having food sensitivities or intolerances. The reliability of saliva testing depends on knowing the correlation or differences between the salivary and blood concentrations, activity, or constituents of a particular substance. The transfer of substances from blood into the saliva or vice versa is dependent on their physiochemical properties. Faster transfer rates of molecules are associated with small molecular weight and great lipid solubility.

A good correlation exists between the saliva/blood ratio of substances and salivary pH. Salivary flow rate and any existing pathophysiology of the oral cavity have also been shown to affect salivary distribution of substances. Saliva content of antigens and antibodies reflects the nutritional and metabolic status of the body, as well as the metabolic, hormonal, biochemical, physiological, immunological or even emotional, status of the individual animal.

Food sensitivity testing for common offending allergens and peptides in dogs or cats is achieved. The sensitivity and testing is for grains most often associated with inflammatory bowel disease ("leaky-gut syndrome, intestinal dysbiosis) or and other symptoms of adverse food reactions—such as, but not limited to wheat and other glutens, corn and soy. These three grain types are among the major constituents (top 5 ingredients) that make up the bulk of standard commercial pre-processed and pre-compounded kibble fed to most dogs or cats. Another common allergen in pet foods or animal food compositions is beef, and the testing and screening is also directed to but not limited to other meats, fish, dairy, eggs, other grains, botanicals, oils from seeds or fish, botanicals, vegetables, or fruit.

The disclosure uses a species-specific test for companion animals such dogs or cats, and other animal species, and the appropriate methods.

This disclosure relates to a diagnostic test system for screening or testing for sensitivity or intolerance to pet food constituents or compositions for a domestic animal, particularly for a dog or cat, and for other species, such as food and fiber animals, and horses.

In particular, the disclosure relates to a diagnostic test system for screening or testing for sensitivity or intolerance of a complete food or food supplements in a dry form, semi-dry form, powdered, or a wet form integrated with functional or nutraceutical compounds from plant or other origins.

The disclosure relates to a diagnostic test system for screening or testing for sensitivity or intolerance to different botanicals or other micronutrients. The activity and the efficacy of the botanicals or other micronutrients depend upon the individual genetic make up of an individual.

The disclosure is further described in detail.

DETAILED DESCRIPTION OF THE DISCLOSURE

There is a need to facilitate the choice of a pet food to suit selected animals so that there is compatibility between the pre-prepared balanced and integrated food composition or mixture of macro- and micro-ingredients and the physiological, metabolic, biochemical or genetic makeup of the pet or companion animal. Most companion animals are fed commercially pre-mixed, pre-compounded, or constituted macro- and micro-ingredients such that there is a single integrated food with such pre-mixed and pre-integrated ingredients. This is usually stated to be the complete or main stay or basic food or diet for the companion animal. Thus, normally such companion animals receive as their regular so-called healthy and nutritious diet one or more regular pre-packaged mixtures of ingredients in commercially prepared foods.

This is largely different to human diets which are generally not pre-packaged as a complete single food with the necessary macro- and micro-ingredients for a complete and healthy diet. Instead the human diet is typically formed with variety and is selected from multiple ingredients which are assembled by choice or purpose, and specifically prepared and cooked on a custom basis according to the individual choice and preference of a human, and specifically for different meals or meal combinations.

The food ingredient or ingredients for which the method of the disclosure is performed is contained in a composition being at least one of a pre-processed food composition, balanced diet or recipe composition. The testing is performed to identify which ingredient(s) from that group of pre-packaged and pre-mixed companion animal foods create sensitivity or intolerance. This can be a moist or semi-moist food, dry kibble or an extruded cereal product. The majority of companion animals or pets in developed countries are fed by this commercially generally available off the shelf pre-prepared pet food mixtures. Sensitivities or intolerances to these foods often arise, but there is no simple manner of determining which ingredient(s) in those foods causes the sensitivity or intolerance.

The present disclosure permits for integrated single stage testing steps for multiple antigens following the intake of a pet or companion animal multi-ingredient food product. The single stage bodily fluid test, tests for multiple antigens in the food product.

In one form of the disclosure, the companion animal is tested by giving such a food being a pre-prepared integrated pre-mixture of ingredients containing the multiple macro- and micro-ingredients for the animal. Then the animal is subjected to at least one of the testing and diagnostic procedures. In this manner it is possible to determine which ingredient(s) in a pre-processed food composition, balanced diet or recipe induces a possible sensitivity or intolerance issue. An assessment is made as to whether different pre-processed or pre-packaged food compositions, balanced diets or recipes are available to offer more appropriate, compatible food(s). In some cases it may necessary to determine whether a special diet needs to be formulated without the offending ingredient or ingredients.

Food sensitivity or intolerance has an immunological basis. It is not possible to distinguish a food which elicits an immunological response from the related intestinal disease or disorder that reflects the body's reaction to the food ingredient or ingredients. The description provided is primarily related to detecting immunologic food sensitivities or intolerances in animals.

A primary example of an immunologic food sensitivity or intolerance is sensitivity to wheat or other gluten foods, for example barley, rice, millet, and oats. In the Irish Setter breed, for example, wheat-sensitive enteropathy is a heritable condition. Immunological reactions to gluten foods causes atrophy of the intestinal villi and inflammation of the small intestine, which, in turn, results in diarrhea and weight loss from malabsorption of fluid, electrolytes, and dietary nutrients. Even though chronic or intermittent diarrhea and intermittent vomiting are the most common symptoms of this food sensitivity, there have been few studies of the prevalence of this condition in animals being presented to veterinarians with chronic diarrhea or vomiting or other common gastrointestinal symptoms. Furthermore, beyond costly measurements of serum IgE-mediated antibodies, there are no adequate methods in veterinary medicine to diagnose or noninvasively test for immunologic food sensitivities or intolerance. This frequently results in either no diagnosis or the missed diagnosis of an immunologic food sensitivity or intolerance.

Despite this situation, many animals with gluten or other food sensitivity or intolerance do not have diarrhea or weight loss, but instead have other signs and symptoms such as vague abdominal pain, nausea, abdominal bloating, flatulence, chronic fatigue, constipation, poor growth and maturity, iron deficiency anemia, osteoporosis, seizures or other neurologic disorders, or even just elevated serum liver enzyme levels. Some animals may be asymptomatic.

Furthermore, animals with gluten or other food sensitivity or intolerance may not have fully developed intestinal lesions. Therefore, the immunologic food sensitivity or intolerance of these animals may not be properly diagnosed using known testing methods, such as endoscopic intestinal biopsy and blood or serum testing. Additionally, these animals may present with other immunologic diseases such as the autoimmune diseases of skin, liver, joints, kidneys, pancreas, and thyroid gland, or microscopic colitis.

One form of the disclosure relates to a method for diagnosing an immunologic food sensitivity or intolerance in a companion animal comprising the steps of firstly collecting a saliva sample; screening the saliva sample to detect the presence of at least one of an IgA, IgM or IgG antibody to a particular food ingredient or composition. Diagnosing an immunologic food sensitivity or intolerance based on the presence of the antibody, is then effected.

Secondly a test involves collecting a blood sample; and preparing serum from the sample; screening the serum sample to detect the quantitative presence of at least one of an IgA, IgM or IgG antibody or immune complex to a particular food ingredient or composition. Diagnosing an immunologic food sensitivity or intolerance based on the presence of the antibody or immune complex is affected.

In some cases the first step is selectively divided into two stages, the first stage being a qualitative step to determine the sensitivity, followed by a quantitative step.

This disclosure is based on an Enzyme-Linked Immunosorbant Assay (ELISA), or other immunoassay platforms such as but not limited to lateral flow, or latex or bead agglutination, which measures the presence of at least one of IgA, IgM or IgG antibodies or immune complexes against a wide variety of foods or food supplements or food additives in an animal's serum, as well as at least one of IgA, IgM or IgG antibodies in an animal's saliva or other bodily fluid.

The current disclosure measures at least one of, and preferably more than one of serum IgA, IgM or IgG or immune complexes that are mediated by complement. Also, at least one of, and preferably more than one of salivary or other bodily fluid IgA, IgM or IgG is measured.

The amount of these antibodies in serum and saliva or other bodily fluid of healthy individual animals is compared to that in serum and saliva or other bodily fluid of animals with clinically expressed or suspected pre-clinical or latent food sensitivity or intolerance.

One method associated with the disclosure is for diagnosing an immunologic food sensitivity or intolerance in companion animals which comprises the steps of: collecting a blood sample; preparing serum from the sample; screening the serum sample to detect the presence of at least one of, and preferably more than one of an IgA or IgG antibody or immune complex to a particular food ingredient or composition. Thereafter there is a diagnosis of an immunologic food sensitivity or intolerance based on the presence of the antibody or immune complex. Another method associated with the disclosure is for diagnosing an immunologic food sensitivity or intolerance in companion animals comprising the steps of: collecting a saliva sample; screening the saliva sample to detect the presence of at least one of, and preferably more than one of an IgA or IgM or IgG antibody to a particular food ingredient or composition. Thereafter there is a diagnosis of an immunologic food sensitivity or intolerance based on the presence of the antibody.

Another method associated with the disclosure is for diagnosing an immunologic food sensitivity or intolerance in companion animals comprising the steps of: collecting a saliva sample; screening the saliva sample to detect the presence of at least one of, and preferably more than one of an IgA or IgM or IgG antibody to a particular food ingredient or composition.

Thereafter there is a diagnosis of an immunologic food sensitivity or intolerance based on the presence of the antibody, and collecting a blood sample; preparing serum from the sample; screening the serum sample to detect the presence of at least one of, and preferably more than one of an IgA, IgM or IgG antibody or immune complex to a particular food ingredient or composition.

Thereafter there is a diagnosis of an immunologic food sensitivity or intolerance based on the presence of the antibody or immune complex.

The immunologic food sensitivity is at least one of wheat or other gluten sensitivity or intolerance, corn or soy, beef or other meat or fish protein sensitivity or intolerance or dairy, eggs, other grains, botanicals, oils from seeds or fish, botanicals, vegetables, or fruit sensitivity or intolerance.

The food ingredient for which sensitivity or intolerance is being tested is contained in at least one mixed ingredient food having multiple ingredients in varying amounts of a premixed food composition, balanced diet or recipe.

The companion animal is tested by giving such a mixed food to the animal. The animal is then tested and a sensitivity or intolerance diagnosis is made by determining the reaction of the animal to different foods and specific selected ingredients. In this manner it is possible to determine whether there is and if so which ingredient in a preprocessed food composition, balanced diet or recipe is a potential or real sensitivity or intolerance problem for a specifically tested animal. An assessment is made as to whether it is possible to use a different preprocessed mixed food composition, balanced diet or recipe, or whether a special diet needs to be formulated without the offending ingredient or ingredients.

The test methodology of the present disclosure differs significantly from all others available for use in animals. It is highly reproducible and clinically relevant. In serum, the food antigen or peptide being tested and at least one of, and preferably more than one of any specific IgA or IgG antibody in serum bind to each other and then fix complement. In saliva or other bodily fluid, the food antigen or peptide being tested reacts directly with the IgA or IgM antibody in the test animal's saliva or other bodily fluid. Common animal food antigens (such as wheat or other glutens, corn and soy, beef or other meats, fish or other foods and botanicals) are bound to wells in a 96-well standard ELISA microtiter plate so that they are non-reactive until an animal's serum or saliva or other bodily fluid is added. Specific binding of IgA or IgG antibody or immune complexes in serum or IgA or IgM antibody in saliva or other bodily fluid to specific food ingredients are identified by finding increased levels of one or more of these antibodies in test, unhealthy or suspect individuals in comparison to healthy control animals.

In another embodiment, the salivary or other bodily fluid testing uses a quantitative point-of-service (P-O-S) test kit system, whereby the animal owner or veterinarian or other designated tester collects the saliva or other bodily fluid from individual healthy animals or unhealthy or suspect animal patients. The requisite biological sampling swabs or straws are provided in the P-O-S test kit; the collected saliva or other bodily fluid is added to the test kit chamber, and the chamber is sealed and submitted to the testing laboratory for quantitative analysis. This is a single stage test for multiple antigens.

In another embodiment, the salivary or other bodily fluid testing uses a quantitative point-of-service (P-O-S) test kit system, in which the requisite salivary or other bodily fluid biological sampling swabs or straws are provided. The collected saliva or other bodily fluid is added to a special well in the test kit chamber, which is then allowed to react by capillary attraction with a series of microchannels containing various food antigens or peptides of interest within the chamber's lateral flow device. Once the reaction is completed, the chamber is sealed and submitted to the testing laboratory for quantitative analysis. This is a single stage test for multiple antigens.

In a further embodiment, the salivary or other bodily fluid testing uses a qualitative point-of-service (P-O-S) test kit system, in which the requisite salivary or other bodily fluid biological sampling swabs or straws are provided. The collected saliva or other bodily fluid is added to a special well in the test kit chamber or dipped into a test strip, which is then allowed to react by capillary attraction across a reagent strip containing various food antigens or peptides of interest within the strip, much like the existing urine dip-stick technology strips, routinely used in human and veterinary medicine. Once the reaction is completed, qualitative reactions are read on a color-grading scale provided with the kit. These reactions can range from negative or little to no color reaction to a highly reactive intense color development. This is a single stage test for multiple antigens.

Positive qualitative reactions seen with the P-O-S test kit can help to identify the major food reacting antigens or peptides in an animal's saliva or other bodily fluid, but should be confirmed by one or more of the quantitative serum or saliva or other bodily fluid tests described in this disclosure. This is a single stage test for multiple antigens.

For quantitative testing, an animal's serum or saliva or other bodily fluid is added to the ELISA microtiter plate or other immunoassay platforms such as but not limited to lateral flow, or latex or bead agglutination, which measures the presence of IgA, IgM or IgG or immune complexes against a wide variety of foods or food supplements or food additives in an animal's serum, as well as in an animal's saliva or other bodily fluid and any specific antibodies present directed against IgA, IgM or IgG antibodies or immune complexes (serum) or IgA, IgM or IgM antibodies (saliva) or other bodily fluid are then bound to their respective food antigens or peptides. The plate is washed and an enzyme conjugate is added that recognizes the bound antibodies of IgA, IgM or IgG or immune complexes in serum, and IgA or IgM in saliva or other bodily fluid. After incubation and washing, substrate is added to visualize the bound antibodies of IgA, IgM or IgG or immune complexes in serum, and IgA or IgM or IgG in saliva or other bodily fluid. The amount of the optical density recorded is proportional to the amount of bound antibody to IgA, IgM or IgG or immune complexes in serum, and IgA or IgM or IgG in saliva or other bodily fluid. A report depicting these reactions is plotted on a simple bar graph. Results show with a high degree of accuracy if an animal patient has a positive or negative reaction against a particular food ingredient.

Food Sensitivity or Intolerance Reactions

Research to date has shown that serum IgA or IgG alone, or with complement, constitute the main immunologically reactive pathways of foods and food supplements. In saliva or other mucosal secretions or other bodily fluids such as tears or milk, the main immunologic reactants are IgA or IgM. These reactive immune responses are characterized classically as Types I, II, III, and IV hypersensitivities.

Type I immune reactive responses are mediated by IgE antibody, and are commonly called an immediate hypersensitivity. This allergic reaction occurs within two hours of allergen exposure or ingestion.

Type II immune reactive responses are mediated by IgG or IgM antibodies and are commonly called delayed hypersensitivity. The allergic reaction occurs from two hours to several days after allergen exposure.

Type III hypersensitivity responses form an immune complex that is also a delayed hypersensitivity, because the allergic reaction occurs days to weeks post allergen exposure or ingestion. Type III reactions develop when immune complexes, typically of the IgG class form in such large quantities that they cannot be cleared adequately by the reticuloendothelial system. Allergen exposure results in production of IgG, which then binds to the allergen, forming immune complexes in the blood. These immune complexes in turn activate complement, resulting in the covalent binding of complement component C3b to the IgG, thereby forming immune complex-C3b. The immune complexes so formed are deposited at various sites throughout the body, and damage ensues when they are deposited and further activate complement, producing and releasing inflammatory cytokines. Release of cytokines causes leukocytes to release proteases, mast cells and vasoactive amines that damage blood vessels and escalate the inflammatory process.

Type IV immune reactive responses represent the cell-mediated form of delayed hypersensitivity. The allergic reaction occurs days to weeks after allergen exposure. The most serious type of delayed hypersensitivity is a granulomatous tissue rejection, which occurs when macrophages ingest but cannot degrade an offending allergen, thereby resulting in persistent stimulation of tissue macrophages. Stimulated macrophages elaborate cytokines that cause the macrophages and other cell types to concentrate around and in the area of tissue injury. T-lymphocytes are then stimulated in turn by cytokines, which activate complement and induce immune-complex formation.

Measuring IgE remains the standard for determining the presence of inhalant allergies (atopy), but this method usually fails or is too costly when diagnosing food sensitivity or intolerance as related to chronic diseases.

Delayed food-related sensitivities begin in the gastro-intestinal tract when the intestinal lining becomes hyperpermeable. This problem is known as "leaky gut syndrome" or intestinal dysbiosis, and is defined as an increase in permeability of the intestinal mucosa to partially digested protein macromolecules, micromolecules, antigens and toxins. The immunological reaction to these proteins or other molecules in the liver initiates and perpetuates chronic food sensitivity or intolerance. When the gut is unhealthy, the rest of the body is unhealthy. The disease process that ensues is typically chronic or intermittent and often involves the gut and skin, as well as internal organs such as the liver. Gastro-intestinal tract function is disrupted when the lining of the gut is inflamed or damaged. With a leaky gut, large food antigens can be absorbed into the body. The body's defense systems then attack this antigen or antigens and the result is the production of antibodies against what was once a harmless, innocuous food ingredient. These IgA or IgG antibodies and immune complexes are formed in the bloodstream and circulate throughout the body where they can damage other tissues along the way. In saliva or other bodily fluid, these reactants are typically IgA or IgM.

Immune Complex

Immune complexes containing large food antigens enter the blood from the gastro-intestinal tract then travel through the liver where most immune complexes are removed. However, if circulating immune complexes pass the liver filtering system, they may cause injury to many body tissues. Malabsorption of food particles from the gastro-intestinal tract can also travel by lymphatic drainage to the body. The lymph channels in the gut wall converge at the thoracic duct which drains its contents into the large thoracic veins. This combination of antibody with complement in the blood stream becomes a circulating immune complex. Immune complexes subsequently attach to receptors on red and white blood cells and then these altered cells are cleared by the body's liver or spleen (reticuloendothelial system).

Any circulating immune complexes that are not removed by the reticuloendothelian system of the liver (or spleen) can activate the complement cascade. Individuals with more immune complexes on their red blood cells are the ones that suffer from chronic food sensitivities or intolerances.

Circulating immune complexes also can damage the integrity of blood vessel capillaries which in turn can trigger inflammatory events.

Diagnosing Immunologic Food Sensitivity or Intolerance by Blood or Saliva Testing Samples for Antibodies or Immune Complexes A blood serum or saliva or other bodily fluid sample from the animal patient is shipped to the laboratory for testing. Although this is one method for collecting a sample from a patient, it is recognized that other methods of obtaining a sample may be used within the scope of the disclosure. Such methods include taking the patient physically to a veterinary clinic or laboratory to collect a blood sample to prepare its serum or a saliva or other bodily fluid sample, or, could include a P.O.S. qualitative saliva or other bodily fluid screening test performed by the pet owner or veterinarian or other person.

Once collected at or received by the lab, the blood serum or saliva or other bodily fluid sample is then screened using the ELISA method or other immunoassay platforms such as but not limited to lateral flow, or latex or bead agglutination, which measures the presence of selected IgA or IgG antibodies or immune complexes against a wide variety of foods or food supplements or food additives in an animal's serum, as well as IgA or IgM antibodies in an animal's saliva or other bodily fluid. The detection of a particular antibody in the patient serum or saliva or other bodily fluid at a level higher than that seen in healthy animal patients then forms the basis for a diagnosis of the food sensitivity or intolerance associated with that antibody.

In one form there is provided a diagnostic test system for screening or testing for food sensitivity or intolerance in animals of the food composition which can comprise at least several active components of wheat or other gluten foods, corn, soy, beef or but not limited to other meats, fish, dairy, eggs, other grains, botanicals, oils from seeds or fish, botanicals, vegetables, nuts, or fruit sensitivity or intolerance.

In another form there is provided a diagnostic test system for screening or testing for food sensitivity or intolerance in animals of other constituents including a group of and at least macro- and micro-components such as vitamins, amino acids, and one or more plant, part of plants and plant extract(s) having functional and nutraceutical properties.

There is also provided a diagnostic test system for screening or testing for food sensitivity or intolerance in animals of the activity of one or more protein compounds, depending upon the food ingredients, the physiology of the animal's digestive tracts and the individual genetic make up of the animal.

There is provided a diagnostic test system for screening or testing for food sensitivity or intolerance in animals that individually respond with an immune reactive response to functional, nutraceutical or therapeutic compounds, and which depends upon the genetic make up of the animal, which differs from the ability to adapt to the environment and to interact with nutrients.

There is provided a diagnostic test system for screening or testing for food sensitivity or intolerance in animals that the activity and the efficacy of functional, nutraceutical and therapeutic compounds of plant or other origin depends upon their molecular dietary signature, which is related to the individual genetic make up, according to the concept of nutrigenomics.

The immune reactive response of a pet animal is dependent upon its genetic make up that is the coordinated and integrated relationship among genes which can be differently regulated from botanicals or other compounds, according to the individual genotype; the gene(s) act downwards (down-regulated) and upwards (up-regulated) in the regulation of molecular, cellular and biological pathways.

There is provided a diagnostic test system for screening or testing for food sensitivity or intolerance in animals that wherein the adverse immunologic reaction effect of the ingredients can also vary according to the genotype of pet animals, and the variability of individual animals.

The compounds and food ingredients can induce a variable reactive immune response to the physiological or pathological response of an individual pet animal. This can be expressed by what is termed "leaky gut syndrome" or intestinal dysbiosis. Furthermore, the gut dysbiosis in turn can lead to damage or malfunction of other body tissues, especially the skin. This is termed the "gut-skin connection."

The term "pet" means a domestic dog, cat or horse. The term "pet food composition" means a food composition or feed ingredient that is intended for ingestion by the pet. Pet food compositions may include, without limitation, nutritionally balanced compositions suitable for daily feed, as well as supplements which may or may not be nutritionally balanced.

The pet food compositions that induce adverse immune reactions or food sensitivities may be prepared by any of a variety of processes. The components may be obtained from plant or vertebrate animal matter, or otherwise provided, and then subjected to pet food processing, as meal, pellet, cold extrusion, heat extrusion autoclaved tins and pouches.

There is provided a diagnostic test system for screening or testing for food sensitivity or intolerance in animals, of the offending food ingredients being in preprocessed or pre-mixed pet food meals, biscuits, snacks, treats, sprinkles, candies and other form of foods.

The ELISA testing system, or other immunoassay platforms such as but not limited to lateral flow, or latex or bead agglutination, are well known in the art. These assays measure the presence of selected IgA or IgG antibodies or immune complexes against a wide variety of foods or food supplements or food additives in an animal's serum, as well as IgA or IgM antibodies in an animal's saliva or other bodily fluid. The presence of these IgA or IgG antibodies or immune complexes in a patient's serum is tested against one or more of a selected panel or group of food antigens or ingredients. The presence of IgA or IgM antibodies in saliva or other bodily fluid is also tested against one or more of a selected panel or group of food antigens or ingredients. If the results show an increased level of any of these selected antibodies to food antigens or ingredients in the serum or saliva or other bodily fluid of a patient in comparison to those levels of the same selected antibodies in healthy animals, the findings indicate that the animal patient does in fact have a particular immunologic food sensitivity or sensitivities or intolerance. The animal patient should then be treated accordingly by removing the triggering substance or substances from the diet or by other methods known in the art.

Although specific parameters and equipment have been discussed in this aspect of the disclosure, it is understood that the parameters may differ and that different equipment may be used to carry out the disclosed methodologies without deviating from the scope of the disclosure.

This blood serum or saliva or other bodily fluid testing method may be combined with one or more other immunologic food sensitivity or intolerance diagnostic indicators previously described according to other established methods in order to further enhance the sensitivity and accuracy of immunologic food sensitivity or intolerance diagnosis.

Secretory IgA serves as a mucosal barrier to certain macromolecules, bacteria, and viruses. When these molecules or organisms interact with secretory IgA and the mucosa, their entrance and exposure to the gut-associated lymphoid tissue (GALT) is blocked. This blockage permits the host to shield efficiently the systemic immune response, local immune response, or both, from onslaught of foreign molecules.

Secretory IgA therefore has anti-bacterial, anti-fungal, and anti-viral activities, and plays an important role in protection of mucosal surfaces from adherence of microorganisms.

Another important role of secretory IgA is in prevention of the diffusion of food antigens into mucous membranes.

Despite the enteric route of exposure to food antigens and peptides, food-specific antibodies are typically measured only in blood, and not in saliva or other bodily fluid.

The disclosure includes using a bodily fluid of a companion animal such as saliva to determine food sensitivity of that animal. Saliva is an accessible fluid, easy to collect, and demonstrates representative responses in secretions after enteric or intragastric antigenic challenge The disclosure includes measuring at least one of, and preferably more than one of salivary or other bodily fluid IgA or IgM against different food antigens and peptides for use in determining food allergy and food intolerance in companion animals.

A method for determining the presence of food allergy or food intolerance in a companion animal such as a dog or cat or horse includes (a) determining at least one of, and preferably more than one of the level of salivary or other mucosal or other bodily fluid IgA or IgM antibody or antibodies against a dietary antigen or peptide present in a food in a saliva or other mucosal or other bodily fluid sample from the animal; and (b) comparing the level determined in step (a) with normal levels of the antibody or antibodies in the mucosal or other bodily fluid sample.

The possible outcomes for the comparison include (i) lower than normal levels or about normal levels of dietary antigen antibodies indicate optimal conditions; and (ii) higher than normal levels of dietary antigen antibodies indicate a food allergy or food intolerance.

There is a also a method for determining a type of antibody in a presence of food allergy or food intolerance to a food in an animal, comprising (a) determining a level of antibodies against a dietary antigen or peptide present in the food in a first saliva or other mucosal or other bodily fluid sample from the animal patient; (b) determining a level of antibody or antibodies against cross-reactive tissue antigen or antigens or peptides present in a second salivary or other mucosal or other bodily fluid sample from the animal patient, wherein the first and second samples are the same or different; and (c) comparing the level of antibody or antibodies determined in steps a) and b) with normal levels of the antibody or antibodies found in healthy animals.

The possible outcomes for the comparison include (i) essentially normal levels of antibody or antibodies against the dietary antigen or peptide and normal levels of antibody or antibodies against cross-reactive tissue antigen or peptide indicate optimal conditions; (ii) higher than normal levels of antibody or antibodies against the dietary antigen and essentially normal levels of antibody or antibodies against cross-reactive tissue antigen or peptide indicate food allergy and intolerance without cross-reacting to tissue antigen or peptide; (iii) essentially normal levels of antibody or antibodies against the dietary antigen or peptide and higher than normal levels of antibody or antibodies against cross-reactive tissue antigen or peptide indicate an autoimmune reaction not related to the dietary antigen or peptide; and (iv) higher than normal levels of antibody or antibodies against the dietary antigen or peptide and higher than normal levels of antibody or antibodies against cross-reactive tissue antigen or peptide indicate a presence of food allergy and intolerance resulting in an autoimmune reaction.

A test informs a pet owner of clinical conditions of their pet who may suffer from food sensitivities, allergies or food intolerance. The test uses a method that measures antibody titers to dietary antigens. The test method measures the antibodies' ability to bind to a recombinant antigen, synthetic peptide, a peptide prepared by enzymatic digestion corresponding to the dietary antigen, or different cross-reactive tissue antigen or antigens.

There is an immunoassay for detecting food allergies and food intolerance in a patient using mucosal or other bodily fluid secretions. Mucosal secretions are secretions of a mucosa, such as saliva.

Forms of biological fluid, other than saliva, for instance urine, tears, or milk or other mucosal secretions can be used.

There is a method for detecting food allergies and food intolerance in an animal. The method includes (a) determining a level of antibody or antibodies against a dietary antigen or peptide in the food in a salivary or other mucosal or other bodily fluid sample from a patient; and (b) comparing the level determined in step (a) with normal levels of the antibody or antibodies in the salivary or other mucosal or other bodily fluid sample.

The possible outcomes for the comparison include (i) lower than normal or essentially normal levels of antibody or antibodies to dietary antigen or peptide indicate optimal conditions; and (ii) higher than normal levels of antibody or antibodies to dietary antigen or peptide indicate a food allergy or food intolerance.

The detection of antibodies can be performed with an immunoassay. Immunoassays include, but are not limited to, ELISA test, RIA test, latex agglutination, beads assay, and proteomic assays. A preferable immunoassay is the ELISA test. Other immunoassays can be used and the choice of immunoassay can be determined by one of ordinary skill in the art.

A normal reading is derived from a baseline measurement taken from antibody measurements for individuals without symptoms relating to food allergies or food intolerance. A baseline measurement for the test is obtained by observing the antibody measurements for individuals without symptoms relating to food allergies or food intolerance. For example, most readings for antibody measurements from an individual without symptoms relating to food allergies or food intolerance are below a certain reading. Preferably, about 50-100% of the readings from an animal without symptoms relating to food allergies or food intolerance are below the certain reading, more preferably about 60-100%, 70-100%, or 80-100% of the readings, even more preferably about 90-100% of the readings. If an animal exhibits antibody measurement two standard deviations above the baseline, the above-normal antibody measurement indicates the presence of food allergy or food intolerance.

Additionally, antibodies against cross-reactive tissue antigen or antigens may be tested. Cross-reactive tissue antigen or antigens include, but are not limited to, lectins, lectins receptors, tropomyosin, smooth muscle, epithelial cell antigens, enzymes, cytochrome P-450 enzymes, and transglutaminase. Ingested dietary antigens or peptides may induce antibodies that react with the specific dietary antigen and another antigen, such as a cross-reactive tissue antigen. If antibodies against cross-reactive tissue antigens are tested in addition to the dietary antigens, then the antibodies can be determined to be protective or pathogenic.

Essentially normal levels of antibodies against the dietary antigen or peptide and normal levels of antibodies against cross-reactive tissue antigen or antigens indicate optimal conditions. Higher than normal levels of antibodies against the dietary antigen or peptide and essentially normal levels of antibodies against cross-reactive tissue antigen or antigens indicate food allergy and intolerance without cross-reacting to tissue antigen or antigens. Essentially normal levels of antibodies against the dietary antigen or peptide and higher than normal levels of antibody or antibodies against cross-reactive tissue antigen or antigens indicate an autoimmune reaction not related to the dietary antigen or antigens. Higher than normal levels of antibodies against the dietary antigen or peptide and higher than normal levels of antibodies against cross-reactive tissue antigen or antigens indicate a presence of food allergy and intolerance resulting in an autoimmune reaction.

There can be an apparatus and method for conducting a variety of assays for the determination of analytes in samples. There can be a single-use device designed to be adaptable to a variety of real-time assay protocols, preferably assays for the determination of analytes in biological samples using immunosensors or other ligand/ligand receptor-based biosensor embodiments.

There can be a metered portion of a sample, for precise and flexible control of the movement of a sample or second fluid within the device. The device and method is for rapid in situ determinations of one or more analytes, and single-use methodology that minimizes the risk of contamination of both operator and the animal. As such there is a point-of-service (P-O-S) clinical diagnostic use.

A multitude of laboratory tests for analytes of interest are performed on biological samples for diagnosis, screening, disease staging, forensic analysis, pregnancy testing, drug testing, and other reasons. While a few qualitative tests, such as pregnancy tests, have been reduced to simple kits for home use, the majority of quantitative tests still require the expertise of trained technicians in a laboratory setting using sophisticated instruments.

Optical means for detecting the binding of an analyte to a receptor is employed, or alternatively there can be electrochemical detection, in which binding of an analyte directly or indirectly causes a change in the activity of an electroactive species adjacent to an electrode, has also been applied to immunoassay.

Therefore, there exists within the field of analyte sensing, and in particular for applications in which analytes must be determined within biological samples such as blood, a need for apparatus that can rapidly and simply determine analytes at the P-O-S, and can be performed by less highly trained staff than is possible for conventional laboratory-based testing. It would be of benefit in the diagnosis and treatment of critical veterinary conditions for the veterinarian or veterinary technician to be able to obtain clinical test results without delay. The apparatus should be adaptable to determination of a range of analytes and capable of single-use so that there can be disposal of the sample after testing.

A device according to the present disclosure has the advantage that the sample and a second fluid can contact the sensor array at different times during an assay sequence. The sample and second fluid may also be independently formed with other reagents or compounds present initially as dry coatings within the respective conduits. Controlled motion of the liquids within the device further permits more than one substance to be added into each liquid whenever the sample or fluid is moved to a new region of the conduit.

In operation, an amount of a preferably biological sample is placed into the sample chamber of the device. The device can have reading zones or the device can be placed into a reading apparatus. A metered portion of the sample can be amended with at least one antibody-enzyme conjugate, and is then contacted with the immunosensor. A second fluid, which contains an inactive substrate for the enzyme, is used to rinse the immunosensor substantially free of unbound antibody-enzyme conjugate, and the response of the immunosensor is recorded and analyzed for the presence, or amount of, analyte of interest. The device may contain a plurality of immunosensors and reagents.

After the reading, the operator removes and discards the device. The reader is then ready for another measurement. While the use of the disclosure is frequently referred to in a biological or medical context, it will be appreciated that the present disclosure may be practiced in any situation where it is desired to perform in situ chemical analyses of liquid samples at speeds which approach real-time.

A dipstick test device is used for detecting an analyte in a liquid sample such as saliva or other biological fluid by treating the analyte with at least one liquid reagent to form a detectable reaction product. The device can include: a) an aqueous impermeable, aqueous insoluble reaction zone, adapted to retain the detectable reaction product; and b) a control absorbent above, and in liquid-transferring relation with, the reaction zone. The control absorbent can have predetermined, limited liquid-absorbing capacity, and the dipstick is configured for location with a vessel containing the sample. The control absorbent is above the reaction zone, so that the control absorbent fills with sample and the reaction zone incubates with the sample. The device may further include an absorbent reservoir which can move into liquid transferring contact with the reaction zone.

This device and method is for use for detecting an analyte, for example, using an immunoassay. An analyte in a sample may be detected by treating the sample with various reagents, such as labeled immunological binding partners to the analyte and reagents to enable detection of the label. Often, the sample is washed between administrations of various reagents.

An assay may depend on controlling the amount of reactants exposed to the sample and the duration of the reactions taking place. It is desirable to have the ability to assay small sample volumes with relative low concentrations of analyte, and/or to detect relatively small differentials in analyte concentration. Finally, it is desirable to have a system to permit measuring whole blood samples, serum and saliva or other bodily fluid without complex equipment.

One method for adding and washing reagents in an immunoassay uses an absorbent material to move liquid washes and reagents through a solid substrate such as a membrane to which other reactants are immobilized.

There can be an immunoassay test device including sorbent material for drawing liquid through a microporous membrane at the bottom of a test well. The sorbent material is resiliently biased away from the membrane, and it draws liquid through the membrane only when the two are forced together to overcome the bias. Sorbent material comprises a surface layer which is hydrophobic and a bulk portion which is wettable. Reagents are added serially to the test well and, after each reagent has been in the well for a prescribed time, the membrane and sorbent material are forced together to draw off liquid before the next reagent is added.

Generally there is a dipstick test device for detecting an analyte in a liquid sample such as saliva or other biological fluid by treating the analyte with at least one liquid reagent to form a detectable reaction product. The test device includes two components: a) means defining an aqueous permeable, aqueous insoluble reaction zone, adapted to retain the detectable reaction product; and, integral with or separate from the reaction zone, b) a control absorbent above, and in liquid-transferring relation with, the means defining a reaction zone The control absorbent has a predetermined, limited, liquid-absorbing capacity. The dipstick is sized and configured for insertion in a vessel containing the sample, with the control absorbent oriented above the means defining a reaction zone, so that the control absorbent fills to capacity and the means defining a reaction zone incubates with the sample.

The reaction zone comprises at least one reactant e.g. a specific binding partner for the analyte participating in a reaction to form the detectable product.

The reaction product is detected by visual inspection, and the means defining a reaction zone is visible by external inspection of the device; optionally, the device includes a contrast region surrounding the reaction zone to aid in the assay by contrasting with the reaction zone in respect to a characteristic being assayed; also optionally, the device can include an intensity scale for quantitative detection of sample analyte.

The reaction zone is either integral with the control absorbent or it is attached to a face of the control absorbent The reaction zone can define at least two reaction regions, and the test device comprises means for isolating the reaction regions from each other. At least one reaction region may be a control region.

The device includes an aqueous impermeable face plate having at least one opening to allow liquid to reach the means defining a reaction zone. In order to provide a flush test head, the means defining a reaction zone comprises a flat reagent retention element having a node positioned to extend into each face plate opening.

The test may include a reagent pack sized and configured to supply a plurality of reagents to the reaction zone. For example, the reagent pack may include liquid reagents for generating a detectable reaction product.

The reaction zone can be positioned at one end of an elongated dipstick, and the device further can comprise a filter assembly positioned at an end of the dipstick. The device can include a reaction tray comprising a well for the filter assembly on the dipstick and to retain the filter assembly as the dipstick is removed from the well.

Detecting an analyte in a sample is by reacting the analyte with at least one reagent to form a detectable reaction product. The method can include:

a) providing a test device comprising a control absorbent above, and in-transferring relation with, a defined a reaction zone, the control absorbent having a predetermined, limited, liquid-absorbing capacity; the control absorbent is in liquid-transferring relationship with the defined reaction zone;

b) inserting the dipstick into a vessel containing a predetermined volume of sample, with the control absorbent oriented above the defined reaction zone;

c) incubating the predetermined sample volume with the reaction zone;

d) allowing formation of the detectable reaction product; and e) detecting the reaction product.

Different Criteria for Dogs and Cats

For a healthy control dog or cat, the salivary IgA antibody levels are generally below about 10 U/ml (dog) or below about 25 U/ml (cat). The salivary IgM antibody levels are generally below about 25 U/ml for healthy dog or cat.

For a patient dog or cat with moderate food allergy and food intolerance, at the salivary IgA antibody levels are generally at about 15 U/ml (dog) or at about 30 U/ml (cat). The salivary IgM antibody levels are at about 35 U/ml for patient dog or cat.

For a patient dog or cat with severe food allergy and food intolerance, the salivary IgA antibody levels are generally below about 20 U/ml (dog) or about 35 U/ml (cat). The salivary IgM antibody levels are generally at about 40 U/ml (dog or cat). Most of the readings (about 98%) for the salivary IgA antibody levels in the healthy control dog or cat are under about 10 U/ml (dog) or 25 U/ml (cat). Likewise, most of the readings (about 85%) for the salivary IgM antibody levels in the healthy control dog or cat are under about 25 U/ml. However, there are certain readings in the panel of the healthy control dog or cat that are higher than about 10 U/ml (dog) or 25 U/ml (cat). Particularly higher readings in the healthy control dog or cat may indicate sensitivity to the corresponding dietary antigen.

In the patient dog or cat with moderate food allergy and food intolerance, most of the readings for salivary IgA antibody levels are above about 15 U/ml (dog) and 30 U/ml (cat). In the patient dog or cat with severe food allergy and food intolerance, most of the readings for salivary IgA antibody levels are above 20 U/ml (dog) and 35 U/ml (cat).

The serum antibody can be IgA, IgM, IgG or immune complex. The serum level of at least one of:

(a) about 100 mg/dl (dog), and about 300 mg/dl (cat) of IgA, or (b) about 200 mg/dl (dog) and about 300 mg/dl (cat) of IgM, or (c) about 1750 mg/dl (dog) and about 2500 mg/dl (cat) of IgG; or or a relative increase in the level of immune complex is indicative of at least mild insensitivity or intolerance.

General

Many different formats are possible for carrying the sample bodily fluid to the reaction zone. In some cases the bodily fluid is applied to an appropriate filter paper or other carrier material and the filter paper or other carrier material with that fluid sample is impregnated on and in the paper or other carrier material carrier and is then sent to a laboratory by any convenient means for analysis. The paper or other carrier material including the sample may, for instance, in one part contain saliva or other bodily fluid, and in another separate part there can be serum. By using filter paper or other carrier material as the carrier, it can be easy for an owner of a pet to simply mail a sample to a laboratory for appropriate testing of one or more antigens. The filter paper or other carrier material can have one or more reaction zones for different antigens. This carrier system of filter paper or other carrier material permits for a wholly or partly dehydrated sample to be carried to a laboratory for subsequent processing, which can include a hydration step prior to analysis in an appropriate analyzer.

This carrier system for transmitting samples to a laboratory can have effective application for other clinical tests, for instance, the filter paper or other carrier material could have direct application and be applied to the thyroid testing procedures and processes as fully described in the applications DETECTION AND MEASUREMENT OF THYROID HORMONE AUTOANTIBODIES, filed as application Ser. No. 12/269,866 on Nov. 12, 2008 (Dodds and Ongchangco); DETECTION AND MEASUREMENT OF THYROID HORMONE AUTOANTIBODIES USING EQUILIBRIUM DIALYSIS, filed as Application Ser. No. 61/156,843 on Mar. 2, 2009 (Dodds and Ongchangco) and DETECTION AND MEASUREMENT OF THYROID ANALYTE PROFILE, filed as application Ser. No. 12/430,038 on Apr. 24, 2009 (Dodds and Ongchangco).

In the specification, there have been disclosed typical embodiments of the disclosure. Although specific terms are employed, they are used in a generic and descriptive sense only and not for purposes of limitation, the scope of the disclosure being set out in the claims. It is therefore to be understood that within the scope of the appended claims the disclosure may be practiced otherwise than as specifically described.

What is claimed is:

1. A method for diagnosing food sensitivity in a dog comprising the steps of: collecting a sample of saliva; screening the sample to detect a level of at least one of an IgA or IgM antibody to a particular food ingredient or composition, and diagnosing food sensitivity based on the level of the antibody.

2. The method of claim 1 further comprising collecting a first testing portion of the saliva sample and wherein the first testing portion is the sample for use in the screening step.

3. The method of claim 2 wherein the sample is about 1-3 milliliters.

4. The method of claim 1 wherein the screening step utilizes an enzyme-linked immunosorbant assay (ELISA) testing system to detect the level of the antibody to the particular food ingredient or a panel of particular food ingredients.

5. The method of claim 1 wherein the antibody is IgA or IgM, and the level of at least one of about 15 U/ml of IgA is indicative of food; or a level of about 35 U/ml of IgM is indicative of food.

6. The method of claim 2 wherein the food sensitivity is selected from the group consisting of wheat, corn, soy, gluten, beef, meat, fish protein, dairy, eggs, grains, and botanicals, oils from seeds, fish, vegetables, and fruit.

7. A method for diagnosing food sensitivity in a dog comprising the steps of: firstly collecting a saliva sample; screening the saliva sample to detect a level of at least one of IgA or IgM antibody to a particular food ingredient or composition, diagnosing food sensitivity based on the level of the antibody, and secondly followed by collecting a blood sample; preparing serum from the sample; screening the serum sample to detect the quantitative level of an antibody selected from the group consisting of an IgA, IgM, IgG antibody and immune complex to a particular food ingredient or composition, and diagnosing an immunologic food sensitivity based on the quantitative level of the antibody or immune complex.

8. The method as claimed in claim 7 wherein a first step is divided into two stages, the first stage being a qualitative step to determine food sensitivity, followed by a quantitative step of determining food sensitivity.

9. The method of claim 7 wherein food sensitivity is selected from the group consisting of wheat, corn, soy, gluten, beef, meat, fish protein, dairy, eggs, grains, and botanicals, oils from seeds, fish, vegetables, and fruit.

10. The method of claim 8 wherein food sensitivity is selected from the group consisting of wheat, corn, soy, gluten, beef, meat, fish protein, dairy, eggs, grains, and botanicals, oils from seeds, fish, vegetables, and fruit.

11. The method of claim 1 wherein the food ingredient for which the method is performed is contained in a composition selected from the group consisting of a preprocessed food composition, balanced diet and a recipe composition.

12. The method of claim 7 wherein the food ingredient for which the method is performed is contained in a composition selected from the group consisting of a preprocessed food composition, balanced diet and a recipe composition.

13. The method of claim 8 wherein the food ingredient for which the method is performed is contained in a composition selected from the group consisting of a preprocessed food composition, balanced diet and a recipe composition.

14. The method of claim 1 wherein the antibody is IgA or IgM, and the level of at least one of about 15 U/ml of IgA is indicative of food sensitivity; or a level of about 35 U/ml of IgM is indicative of food sensitivity.

15. The method of claim 1 wherein the antibody is IgA or IgM, and the level of a level below about 10 U/ml of IgA is indicative of food insensitivity; or a level below about 25 U/ml of IgM is indicative of food insensitivity.

* * * * *